United States Patent
Sickels, Jr.

(10) Patent No.: US 8,794,061 B1
(45) Date of Patent: Aug. 5, 2014

(54) APPARATUS, SYSTEM AND METHOD FOR MEASURING THE PROPERTIES OF A CORROSIVE LIQUID

(71) Applicant: Ultra Analytical Group, LLC, League City, TX (US)

(72) Inventor: Robert Eugene Sickels, Jr., Mansfield, TX (US)

(73) Assignee: Ultra Analytical Group, LLC, League City, TX (US)

( * ) Notice: Subject to any disclaimer, the term of this patent is extended or adjusted under 35 U.S.C. 154(b) by 0 days.

(21) Appl. No.: 14/096,444

(22) Filed: Dec. 4, 2013

Related U.S. Application Data (63) Continuation of application No. 14/046,118, filed on Oct. 4, 2013.

(51) Int. Cl.
 *E21B 49/00* (2006.01)
 *G01N 9/26* (2006.01)

(52) U.S. Cl.
 CPC ........................................ *G01N 9/26* (2013.01)
 USPC ........................................ 73/152.05; 73/451

(58) Field of Classification Search
 CPC . G01N 17/008; G01N 17/04; G01N 2009/26; G01N 2009/63; G01N 9/00; G01N 9/36; G01N 9/26; G01N 9/32; G01N 9/12; G01N 9/18; G01N 9/10
 USPC ........................................ 702/9; 73/32 R–454
 See application file for complete search history.

(56) References Cited

U.S. PATENT DOCUMENTS

| | | | |
|---|---|---|---|
| 4,916,426 A * | 4/1990 | Yajima et al. | 338/4 |
| 5,325,716 A * | 7/1994 | Hafner et al. | 73/301 |
| 6,378,362 B1 * | 4/2002 | Dickinson | 73/152.28 |
| 6,687,643 B1 * | 2/2004 | Cason, Jr. | 702/137 |
| 6,712,138 B2 | 3/2004 | Mandal | |
| 7,735,378 B2 | 6/2010 | Singfield et al. | |
| 2004/0200287 A1 * | 10/2004 | Mueller et al. | 73/715 |
| 2009/0056422 A1 * | 3/2009 | Quinn et al. | 73/53.01 |
| 2009/0285721 A1 | 11/2009 | DeGreeve et al. | |
| 2012/0097388 A1 * | 4/2012 | Beck | 166/250.07 |
| 2012/0193090 A1 * | 8/2012 | Lopez De Cardenas | 166/250.01 |

(Continued)

FOREIGN PATENT DOCUMENTS

WO 2012000044 A1 1/2012
WO 2012061872 A1 5/2012

OTHER PUBLICATIONS

Vega, Process pressure/Hydrostatic—Pressure measurement, 35400-EN-090130 from www.vega.com/downloads/BA/35400-EN-Vegawell52ProductInformation.PDF.

(Continued)

*Primary Examiner* — John Fitzgerald
*Assistant Examiner* — Marrit Eyassu
(74) *Attorney, Agent, or Firm* — Colin P. Cahoon; Brandon V. Zuniga; Carstens & Cahoon, LLP (57) ABSTRACT

An apparatus and method used to determine the density and other properties of a corrosive liquid, such as drilling mud. The apparatus uses at least two sensor elements with ceramic facings spaced a known vertical distance apart and inserted into the fluid. The differential pressure measurement provided by these sensors is used to calculate the density of the liquid. This density measurement is then reported in real-time to an operator.

14 Claims, 5 Drawing Sheets

(56) References Cited

U.S. PATENT DOCUMENTS

| | | | |
|---|---|---|---|
| 2012/0204636 A1* | 8/2012 | Teli et al. | 73/309 |
| 2013/0199286 A1* | 8/2013 | Gao et al. | 73/152.27 |
| 2013/0291620 A1 | 11/2013 | Singfield | |
| 2013/0298663 A1 | 11/2013 | Singfield | |
| 2013/0298696 A1 | 11/2013 | Singfield | |
| 2014/0007668 A1* | 1/2014 | Shanks | 73/152.51 |

OTHER PUBLICATIONS

Vega, Process pressure/Hydrostatic—Operating instructions, 35401-EN-111021 from www.vega.com/downloads/BA/35401-EN-VegaWell.PDF.

The Mud Watcher, Transforming Mud Monitoring—Specifications from www.mudautomatics.com.

Red Lion G306 from www.redlion.net/Products/HumanMachineInterface/OperatorInterface/G306.html.

Denver Smart et al. "Micro Motion White Paper" Emerson Process Management, Micro Motion, WP-001243, Rev. B, 2013 from www2.emersonprocess.com/en-US/brands/micromotion/industries/oil-and-gas/oilfield-services/drilling-fluids-management/Pages/Index.aspx.

Auto Wate Drilling Solutions screen shot from www.autowate.com.

Click Koyo, Click CPUs, C0-00DD1-D CPU from www.aboutplcs.com/click/Hardware/CPU-Modules/c0-00dd1-d.html.

Emerson Process Management—Oilfield Services from www2.emersonprocess.com/en-US/brands/micromotion/industries/oil-and-gas/oilfield-services/drilling-fluidsmanagement/Pages/Index.aspx.

MudAutomatics screen shot from www.mudautomatics.com/.

The Mud Weight Watcher, Transforming Weight Control from www.mudautomatics.com/.

Vega—Vegawell 52—Specification Sheet, 34734-EN-0910008 from www.vega.com/downloads/BA/34734-EN-Well52SpecificationSheet.PDF.

Vega—Vegawell 52—Operating Instructions, 4 . . . 20 mA/HART Pt 100, 35402-EN-111021, Document ID 35402.

MezurX Products and Services—Mud SentriX, printed Feb. 27, 2014, located at: http://www.mezurX.Com/Mudsentrix.php, 4 pages.

MD3018 Mud Density Remote Seal Differential Pressure Transmitter for Drilling Mud Density and Cement Density Measurements, Industrial Pressure Products, Specifications, 2005 AMETEK, Inc., 5M0103T (210057).

MD3018 Series Mud Density Transmitter, Installation/User Manual, AMETEK, Revision C, May 2000, pp. 1-14.

MD3018 Mud Density Transmitter—Overview, AMETEK.

* cited by examiner

APPARATUS, SYSTEM AND METHOD FOR MEASURING THE PROPERTIES OF A CORROSIVE LIQUID

CROSS-REFERENCE TO RELATED APPLICATION

This application is a continuation of and claims filing priority rights with respect to currently pending U.S. patent application Ser. No. 14/046,118, filed on Oct. 4, 2013.

BACKGROUND OF THE INVENTION

1. Technical Field

The present invention generally relates to measuring at least the density of a corrosive liquid by using at least two submerged corrosion resistant pressure sensors that are separated by a known vertical distance. The corrosive liquid may be erosive, abrasive, fouling, caustic, basic, acidic, capable of damaging sensors, or any possible combination thereof. In particular, the invention relates to an apparatus, system, and method for measuring the density of a corrosive liquid, such as drilling mud, by using at least two corrosion-resistant pressure sensors submerged in the corrosive liquid and separated by a known vertical distance to obtain at least two pressures at different depths in the corrosive liquid.

2. Background

With the discovery of new drilling techniques such as hydraulic fracturing, the United States is currently experiencing an energy bonanza. In addition to the wells being drilled with new techniques, many more wells are being drilled with tried and true techniques. All told, thousands of wells are being drilled every year in the United States alone. In every one of these wells, drilling fluids such as muds, cements or other slurries play an integral role in ensuring a safe and efficient drilling operation. For example, drilling mud is useful for controlling well formation pressures, removing well cuttings, and facilitating the cementing and completion of wells. Perhaps one of the most important functions of drilling muds is to help to prevent potentially devastating oil well blowouts. However, drilling muds are only effective at preventing blowouts when their properties, such as density, are properly adjusted. Real-time measurement of drilling properties is also used to help the rig operator understand down-hole conditions. Consequently, being able to measure the properties of these fluids while a well is being drilled is critical.

Up until now, traditional mud scales or balances have been used to measure the density (weight) of drilling fluid, cement, or any other type of liquid or slurry. Typically, the mud scales on a drilling site consist of a graduated beam with a bubble level, a weight slider along its length, and a cup with a lid on the end. The cup is used to hold a set amount of liquid to be weighed. The slider weight can be moved along the beam and a bubble indicates when the beam is level. Density is read at the point where the slider weight sits on the beam at level.

Mud scales are calibrated by using a liquid of known density (often water) and adjusting a counter weight. Generally, the scales are not pressurized, but a pressurized mud scale operates in the same manner.

Figure 1:
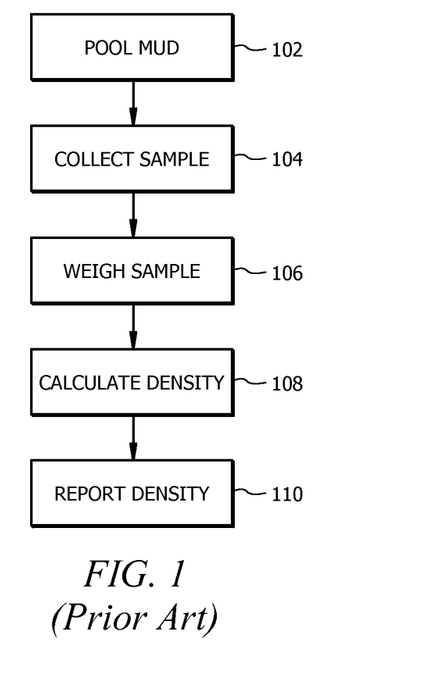
FIG. 1 is a flow chart representation of a prior art process for obtaining the density of a drilling mud.

A method for employing a traditional mud scale will now be described with reference to FIG. 1. First, mud is pooled, for example in a tank, in a pooling step 102. Second, a sample of the mud is collected in a known volume in a collection step 104. Third, the mud is weighed in a weighing step 106 to obtain the mass of the mud. Fourth, the mud's density is calculated in a calculation step 108 using the known volume and the mass of the mud. Fifth, the mud's density is reported to the drilling operator 110. This will permit the drilling operator to make adjustments to the mud's density if it is outside of a desirable density range and can provide useful information on down-hole conditions.

There has been no reliable, real-time method of determining the density of drilling mud. The old mud scale was the most reliable and simple way of making the determination, but it does not provide real-time data. For example, when drilling a well a mud sample typically will be drawn and density will be calculated once every hour for on-shore wells and once every 15 minutes for off-shore wells. Thus, if a mud density fluctuates soon after a sample is taken, it may be 20 minutes before a drilling operator realizes that the density fluctuation has occurred. This in turn may leave little time for implementing corrective measures to keep the mud density in a safe range or for taking other corrective measures to shut a well down. Accordingly, a device capable of measuring mud density in real-time is desirable for the additional safety, reliability, and efficiency it can provide.

Although some existing devices such as Coriolis and Venturi flowmeters can provide real-time density data, they have proven unreliable when operating under the corrosive, erosive, abrasive, fouling, caustic, basic, acidic or other harsh conditions imposed by drilling fluids. Drilling mud is typically made up of water, clay, and additives used to modify the mud's viscosity, density, pH and other properties. The mud creates an environment that is not conducive to prior art sensors. For example, the mud contains solids, including solids in the mud and well cuttings that can be abrasive or erosive. These solids can scrape a sensor and damage it. The mud also tends to be basic, which can damage a sensor by eating away at the sensor. Additionally, the mud can form layers on a surface that are difficult to remove. If the mud forms layers on the sensor, the sensor may become fouled and fail to work properly.

What is needed is a new and innovative device capable of autonomously transmitting real-time density data even under the harsh conditions involved in drilling. For example, a need exists for an apparatus that can measure the density of mud or other liquids every second of every minute during the drilling process and then transmit the measured data to provide operators with density data that is extremely accurate. Accordingly, the risks and liability associated with drilling wells could then be reduced while the reliability and efficiency of the drilling process is simultaneously increased. For example, there would no longer be a need to call out mud weight over intercoms. Instead, operators could receive real time readouts of mud density and have peace of mind that a drilling fluid is operating within a safe density range.

It would also be beneficial if such apparatus were highly energy efficient, using for example, using only 24 watts of power. As a result, the embodiment can run off of back up battery power for long periods between charging by a solar charge. This is desirable for both environmental benefits and cost-savings.

It would also be beneficial if such apparatus were highly portable, comprising, a light-weight, compact unit. Such, a unit could be flown to remote locations by light aircraft or shipped at low costs due to its compact size and light weight. Furthermore, if the unit were constructed from weather-proof components and the mud probes were made from highly durable industrial materials, the unit would be capable of standing up to the rigorous conditions encountered at many drilling sites.

SUMMARY OF THE INVENTION

The present invention generally provides for an apparatus, system, and method for measuring at least the density of a corrosive liquid, for example a drilling mud, by using at least two submerged corrosion resistant pressure sensors that are separated by a known vertical distance. The corrosive liquid may be erosive, abrasive, fouling, caustic, basic, acidic, capable of damaging sensors, or any possible combination thereof. The corrosion resistant sensors may be constructed, for example, from sensor elements that comprise ceramic components. The invention further provides for optionally measuring one or more other liquid properties, for example viscosity, pH, salinity, chloride content, and H2S concentration. The invention further provides for conducting other types of analysis, such as measuring physical or chemical properties.

In a first aspect, the invention provides an apparatus that can measure a corrosive liquid's density by using at least two corrosion-resistant pressure sensors submerged in the corrosive liquid and separated by a known vertical distance to obtain at least two pressures at different depths in the corrosive liquid.

In a second aspect, the invention provides a system comprising a power supply, a Monitor Control Box (MCB) and at least two corrosion-resistant pressure sensors that are spaced a known vertical distance apart in a sensor housing and are in electronic communication with the power supply and the MCB.

In a third aspect, the invention provides a method comprising the steps of pooling a corrosive liquid, inserting into the liquid an apparatus comprising at least two corrosion resistant pressure sensors that are separated by a known distance, using the at least two pressure sensors to detect at least two pressures of the liquid corresponding to a minimum of two different liquid depths that are separated by the known distance, transmitting data comprising the at least two different pressures to a device capable of converting the pressure data to a density, using the device to convert the at least two different pressures into a density for the corrosive liquid, and transmitting a result comprising at least the density for the corrosive liquid.

The inventor has developed a new and innovative device capable of autonomously transmitting real-time density data even under the harsh conditions involved in drilling. For example, one embodiment of the invention can measure the density of mud or other liquids every second of every minute during the drilling process and then transmit the measured data to provide operators with density data that is extremely accurate. Accordingly, the risks and liability associated with drilling wells may be reduced while the reliability and efficiency of the drilling process are simultaneously increased. For example, there is no longer a need to call out mud weight over intercoms. Instead, operators may receive real time readouts of mud density and have peace of mind that a drilling fluid is operating within a safe density range.

Another benefit of the invention is that one embodiment is highly energy efficient, using for example, only about 24 watts of power. As a result, the embodiment can run off of back up battery power for 36 hours in addition to running for 24 hours without a solar charge. This is desirable for both environmental benefits and cost-savings.

Another embodiment of the invention is highly portable, comprising, a light weight compact unit. This unit may be flown to remote locations by light aircraft or shipped at low costs due to its compact size and light weight. Furthermore, because the unit can be constructed from weather-proof components and the mud probes can be made from highly durable industrial materials, the unit is capable of standing up to the rigorous conditions encountered at many drilling sites.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION OF THE INVENTION

Figure 2:
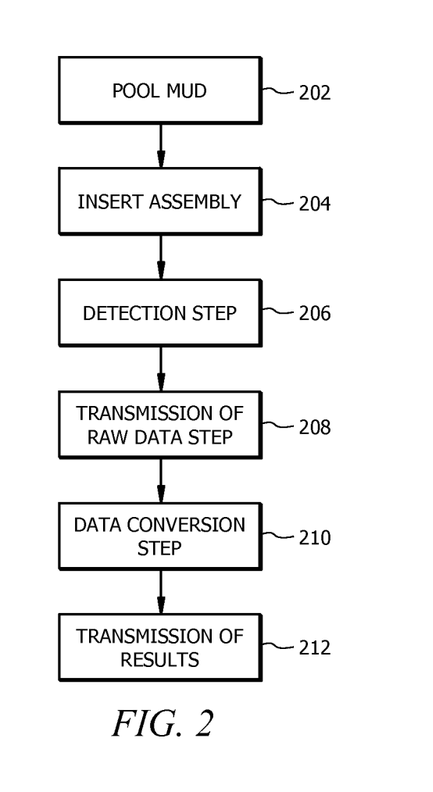
FIG. 2 is a flow chart representation depicting the overall process of one embodiment of the invention.

One embodiment of a method according to the invention will now be described with reference to FIG. 2. First, mud is pooled in a pooling step 202. Second, in an insertion step 204, a sensor assembly comprising at least two corrosion-resistant pressure sensors is inserted into the mud. The pressure sensors are each submerged at a different depth in the mud and separated by a known vertical distance given by subtracting the height of a first sensor in a vertical plane from the height of a second sensor in a vertical plane.

Third, in a detection step 206, the pressures of the liquid at each of the sensors are measured to provide at least two pressures at liquid depths that are separated by the known vertical distance. Thus, the known vertical distance is equal to the difference in the liquid depths of the two sensors.

Fourth, in a transmission of raw data step 208, raw data, including the at least two pressure measurements provided by each of the sensors, are transmitted to a Monitor Control Box ("MCB"). The MCB may comprise, for example, a computational device. The term computational device includes but is not limited to a central processing unit ("CPU"), a programmable logic controller ("PLC") and a computer. Alternatively, the MCB may comprise, for example, a PLC and a computational device. During the transmission of raw data step 208, the raw data is transferred by electronic communication, for example, by wired communication, wireless communication, radio, WiFi, Bluetooth, cable, or optical fiber. In one embodiment, the raw data may be transferred from the sensors to the PLC. For example, the raw data corresponding to pressure measurements may be transferred in a signal. Furthermore, the signal may comprise an electrical current. In one embodiment, a current of 4 milliAmps ("mA") may correspond to a pressure measurement of 0 psi, while a current of 20 mA may correspond to a pressure measurement of 36.26 psi. Currents between 4 mA and 20 mA may correspond to pressure measurements between 0 psi and 36.26 psi. In one embodiment, the PLC converts the raw data from the sensors into pressures. For example, the PLC converts a 20 mA signal into a pressure of 36.26 psi and a 0 mA signal into a pressure of 0 psi. Although, the correlation between the pressures and currents may be different. Likewise, the form of electronic communication used can vary. For example, in another embodiment, the MBC may comprise a computational device in electronic communication with a sensor assembly and a user interface.

Fifth, in a data conversion step 210 at the MCB, the at least two pressures and the known distance are used to calculate the density of the mud. Thus, the pressure measurements from the at least two pressure sensors are convertible into a density measurement of a corrosive liquid. In one embodiment, the at least two pressures from the PLC are transferred to a computer which uses the known distance to calculate the density of the mud. For example, the density can be calculated as follows. Start by subtracting the pressure at a first sensor from the pressure at a second sensor to obtain a pressure differential. Then, calculate the density by dividing the pressure differential by the product of multiplying a unit-of-measurement-appropriate gravitational acceleration constant and the known distance. Alternatively, the density can be calculated by recognizing that given a first pressure sensor at one depth in a liquid, a second pressure sensor at another depth in a liquid, and a fixed vertical distance between two pressure sensors, the differential pressure between the liquid's pressures at the first and second sensors is proportional to the liquid's density. Thus, the density of the liquid is equal to some constant coefficient times the differential pressure of the liquid for given units of measurement. Using this relationship, the coefficient can be calculated by placing the two pressure sensors in a fluid with a known density, and obtaining a differential pressure from sensors separated by the fixed vertical distance. The coefficient is equal to the known density divided by the differential pressure. After calculating the coefficient, the coefficient can be used to calculate a density for a liquid from a differential pressure reading corresponding to sensors separated by a fixed vertical distance in the liquid.

Although in one embodiment the MCB comprises a PLC and a computational device, various configurations of the MCB are possible. For example, in one embodiment, the MCB comprises a device capable of receiving raw data and converting the raw data into a density for a corrosive liquid. In another embodiment, the MCB may be a computational device.

Sixth, in a transmission of results step 212, the density of the mud is transmitted to a user interface. The user interface permits a user to interact with the invention, for example, to access density calculations or other information. The user interface may also permit a user to operate the invention. The user interface comprises a minimum of one device capable of at least receiving information from or transmitting information to the MCB. The user interface may be co-located with the MCB or remote from the MCB. Accordingly, the user interface may be co-located with or remote from a device used to convert the raw data into a density value for the corrosive liquid. For example, a user interface may comprise a control panel, a touchscreen, levers, buttons, dials, a computer, a cellular device, a portable digital assistant, a smart phone or a device that uses audio, visual, tactile, or electronic signals for communication with a user.

A user may comprise at least one person or device. For example, a user may be a drilling operator who uses a user interface to monitor a drilling mud's density. A user may also be a computer, portable device, smart phone, information storage device, a system, a network, or remote corporate offices.

One embodiment of a system according to the invention will now be described with reference to FIG. 3. A power supply 314 is in electronic communication with a sensor assembly 310 and a monitor control box 306 through lines of electronic communication 312 between the power supply 314 and the sensor assembly 310 and between the power supply 314 and the MCB 306. The sensor assembly 310 is also in electronic communication with an MCB 306 through a line of electronic communication 308 between the sensor assembly 310 and the MCB 306. The MCB 306 is in electronic communication with a user interface 302 through a line of electronic communication 304 between the MCB 306 and the user interface 302. Generally speaking, the user interface permits communication between a user and the invention. For example, the user interface 302 may comprise a minimum of one device capable of at least receiving information from or transmitting information to the MCB 306 and receiving information from or transmitting information to a user.

The sensor assembly 310 may comprise at least two sensors. For example, the sensor assembly 310 comprises at least two corrosion-resistant pressure sensors spaced apart by a known vertical distance whose end points correspond to the heights of the at least two sensors. The known vertical distance only includes the vertical component of a distance between the two sensors, but not the horizontal component of the distance between the two sensors. The pressure sensors are at least capable of measuring the pressure of a liquid at two different depths in the liquid. The two different depths correspond to the heights of the at least two sensors and the end-points of the known vertical distance.

In one embodiment, the sensor assembly may comprise two pressure sensors in the form of pressure transmitters with suspension cables. The suspension cables may be fixed relative to each other so that as they suspend the pressure transmitters, the pressure transmitters are also separated by a substantially fixed distance. In another embodiment, the sensor assembly may comprise at least one sensor housing. In another embodiment, the sensor assembly may comprise two sensor housings, wherein the sensor housings both house a separate sensor. The sensor assembly may also comprise other sensors or sensor housings in various configurations.

The sensor assembly 310 is in electronic communication with an MCB 306 through a line of electronic communication 308 between the sensor assembly 310 and the MCB 306. In one embodiment, the MCB 306 may be a computational device. In one embodiment, the MCB 306 may comprise at least a device capable of performing a data conversion step in which a liquid's density is calculated using a constant coefficient corresponding to a known vertical distance and also using two pressure measurements from at least two pressure sensors in the liquid that are separated by the known vertical distance. In another embodiment, the MCB 306 may comprise at least a device capable of performing a data conversion step in which a liquid's density is calculated using the at least two pressures corresponding to at least two different depths in the liquid, the known vertical distance corresponding to the heights of the at least two sensors, and a gravitational acceleration constant. Without wishing to be bound by theory, the gravitational acceleration constant is approximately equal to the gravitational acceleration of an object caused by earth's gravitational field. The gravitational acceleration constant is expressed in appropriate units of measurement, for example approximately 9.80665 m/s$^2$ or 32.174 ft/s$^2$. However, the value used for the gravitational acceleration constant varies depending on the units of measurement used for the at least two pressures and the known vertical distance.

In one embodiment, the MCB 306 may comprise a programmable logic controller ("PLC"), a computational device, such as a computer, and a communication device. In another embodiment, the computer may comprise the communication device. The communication device may be a wired or wireless communication device. The communication device may comprise for example, a device capable of transmitting or receiving information using wired connections, cable, optical fiber, wireless connections, radio, WiFi, or Bluetooth. The communication device may be in electronic communication with at least one user interface 302. The communication device may be in electronic communication with at least one user through the user interface 302. The user may comprise, for example, a human, a device, a computer, a system, or a network. The PLC may be in electronic communication with the at least two sensors. For example, the PLC may be in wired or wireless communication with the at least two sensors.

The sensor assembly 310 is also in electronic communication with the power supply 314 through a line of electronic communication 312 between the sensor assembly 310 and the power supply 314. In the embodiment illustrated in FIG. 3, the power supply 314 comprises at least a device capable of providing the necessary level of power to the sensor assembly 310 and the MCB 306. For example, the power supply 314 may comprise, for example, a power outlet at a drilling site. As another example, the power supply 314 may comprise a power outlet and a power converter. The power supply 314 may alternatively comprise at least one battery box, fuel cell, capacitor, power generator, or other energy storage device. The battery box may comprise, for example, at least one battery. Alternatively, the battery box may comprise a power converter and at least one battery. As another example, the power supply 314 may comprise, for example, a battery box in electronic communication with a solar panel. As another example, power supply 314 may comprise a power converter in electronic communication with the sensor assembly 310, the MCB 306, at least one battery, a solar panel and a communication device. In one embodiment, the power converter is in electronic communication with the communication device. In another embodiment, the battery box may be portable. For example, the power supply or substituent components may be provided with handles or situated on a sled or wheels. In another embodiment, the power supplied to the sensor assembly 310 may come from a power supply 314 connected to the MCB 306. For example, the power supply 314 may be connected to MCB 306 and power may be transferred to sensor assembly 310 by a cable, such as a USB cable. In one embodiment, a single power supply 314 may provide power to the user interface 302, the MCB 306, and the sensor assembly, 310. In another embodiment, each component may have its own power supply. In other embodiments, necessary power may be supplied to the components of the invention by using a variety of different component configurations. For example, various equipment parts, lines of electronic communication, and one or more power supplies may be combined and arranged in a variety of ways.

Figure 3:
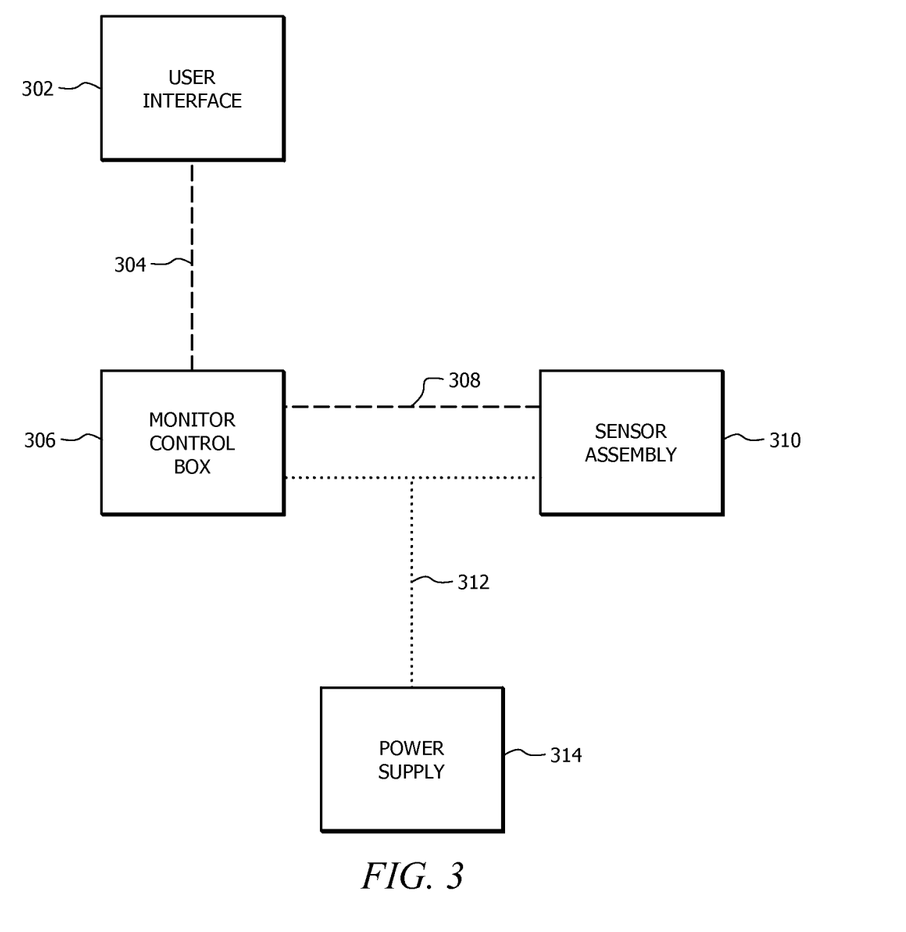
FIG. 3 is a schematic depicting a system that is one embodiment of the present invention.

The inventor anticipates that the equipment and any constituent components discussed in FIG. 3, as well as any auxiliary equipment or components will be used in various configurations. For example, all the equipment may be located in substantially the same location. The equipment may be housed in a housing or not housed. Housed equipment may be housed in a single housing or various components may be grouped together in separate housings. For example, in one embodiment, an MCB 306 is located a distance from the sensor assembly 310. In another embodiment, the MCB 306 is located at the sensor assembly 310. In one embodiment, the PLC may be located at the sensor assembly 310 while the rest of the MBC 306 is located a distance from the sensor assembly 310. As another example, a user interface 302 may be located a distance from the MCB 306. Alternatively, the user interface 302 may be located at the MCB 306. In one embodiment, the power supply 314 may supply all the equipment shown in FIG. 3, alternatively, each piece of equipment or component requiring power may have its own power supply. Likewise, where feasible, a single line of electronic communication, for example a power chord with multiple outlets, may be replaced by multiple power chords and vice versa.

One embodiment of a sensor assembly according to the invention will now be described with reference to FIG. 4A. A sensor assembly 400 comprises a flotation device 404, which may, for example, be a buoy. The flotation device 404 is attached to a sensor housing 410. The sensor housing 410 houses two sensors 408a, 408b separated by a known vertical distance D. The two sensors comprise a first sensor 408a at first height h1 and a second sensor 408b at a second height h2. The known vertical distance D represents the vertical component of the distance between the sensors 408a, 408b. The vertical distance D can be calculated by subtracting the first height h1 from the second height h2. The sensor housing 410 has at least one opening that permits the sensors 408a, 408b to be in fluid communication with a liquid if the sensor housing 410 is submerged in the liquid. For example, if the floatation device 404 is floating on the surface of liquid, the sensors 408a, 408b will both be submerged at different depths in the liquid corresponding to the first height h1 and second height h2, respectively. Because the sensors 408a, 408b are at different depths in the liquid, the first sensor 408a will measure a first pressure that is higher than a second pressure measured by the second sensor 408b. These pressures can then be used in conjunction with the known vertical distance D to calculate the density of the liquid. For example, without wishing to be bound by theory, a liquid's density can generally be calculated as equal to the difference in the first and second presures divided by the product of gravitational acceleration times the known vertical distance D. In performing this calculation, consistent units of measurement must be used. Alternatively, if the known vertical distance D is constant, then the calculation can essentially be reduced to calculating a liquid's density by using conversion factors consolidated in the form of a constant coefficient that converts the difference in the first and second pressure to a density. The coefficient is dependent on the known vertical distance D, but not on a particular liquid composition. For example, the coefficient, 9.6, is derived from the conversion factors necessary to obtain density in pounds per gallon from pressure readings in psig from a first sensor 408a and a second sensor 408b separated by a known vertical distance D of 2 feet. Accordingly, the density of a liquid in pounds per gallon is approximately equal to 9.6 times the difference of the first pressure minus the second pressure where the first and second pressures are given in psig, where the mud density is given in pounds per gallon, and where the known vertical distance between the first and second height is 2 feet. However, if the known vertical distance D changes, the coefficient would need to be recalculated accordingly.

Without wishing to be bound by theory, it is also useful to note that the known vertical distance D is only equal to the actual distance between the two sensors 408a, 408b when the sensors 408a, 408b are oriented along a line that is parallel to the direction of acceleration caused by gravity. If the surface of the liquid is calm and level, then the surface of the liquid will be perpendicular to the direction of acceleration caused by gravity. Accordingly, if the surface of the liquid is calm and level, the flotation device 404 is floating parallel to the surface of the liquid, the sensor housing 410 is attached to the flotation device 404 so that the sensor housing 410 is oriented perpendicular to the surface of the liquid, and the sensors 408a, 408b are oriented along a line that is parallel to the sensor housing 410, then the known vertical distance D will be equal to the actual distance between the two sensors 408a, 408b. However, if the surface of the liquid is disturbed, for example by waves, and the flotation device 404 tilts so that it is no longer perpendicular to the direction of acceleration caused by gravity, then the known vertical distance D will no longer be the actual distance between the two sensors 408a, 408b. Instead, it will be the vertical component of the distance between the two sensors 408a, 408b. For example, if the distance from the first sensor to the second sensor is represented as a vector from the first sensor to the second sensor, and that vector is resolved into a z component that is parallel but opposite to the direction of gravitational acceleration and an x component and a y component that are perpendicular to each other and the z component, then the z-component will be the vertical component of the distance between the two sensors 408a, 408b. Because the actual distance between the two sensors 408a, 408b will remain constant but the vertical component of this distance will change when the flotation device tilts, it may be desirable to employ one or more devices to ensure that the surface of the liquid remains calm and level. Furthermore, it may be desirable to employ a flotation device 404 with a longer radius, length, or width as applicable to the shape of the flotation device 404. Doing so will help to decrease the tilt that the flotation device 404 experiences when floating over a disturbance in the surface of the liquid. Likewise, it may be desirable to employ a gyroscope to prevent tilt.

Alternatively it may be desirable to measure the angle of tilt of the sensors, for example by using a gyroscope, so that the known vertical distance D can be calculated from the measured angle of tilt and the vertical distance between the sensors when the sensors are not tilted. As another alternative it may be desirable to convert pressure readings from the sensors into information regarding the depth of the sensors in a liquid by using a recently calculated density of the liquid. The information regarding the depth of the sensors could then be used to calculate an estimated angle of tilt by employing trigonometry. In calculating an estimated angle of tilt, it may be useful include one or more additional sensors at a fixed distance from one of the two sensors and not in line with the two sensors. For example, next to a first set of two sensors a second set of two sensors may be fixed a known distance from the first set of two sensors. The pressure readings may then be converted to liquid depths at each sensor using recently estimated densities. The liquid depths at each sensor may then be used to obtain an angle of tilt. Other approaches for obtaining an exact or approximate angle of tilt could also be employed.

It is desirable that the at least one opening in the sensor housing 410 permits sufficient fluid communication between the sensors 408a, 408b and the liquid so that the properties of the liquid in contact with the sensors inside the sensor housing 410 are substantially similar to the properties of the liquid outside the sensor housing 410, even if, for example, the composition and the properties of the liquid are constantly changing. This will help to ensure that the properties of the liquid inside the sensor housing 410 as measured by the sensors 408a, 408b are substantially similar to the properties of the liquid outside the sensor housing 410.

Figure 4A:
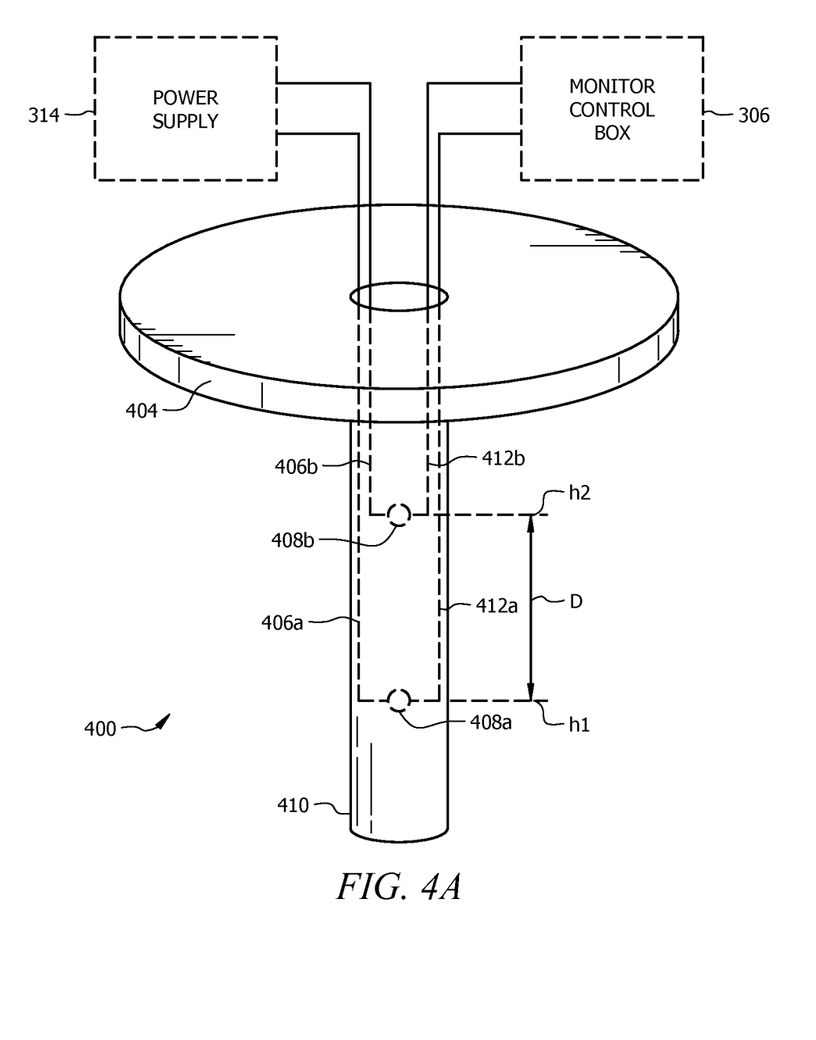
FIG. 4A depicts a perspective view of one embodiment of a sensor assembly according to the invention.

In the sensor assembly 400 depicted in FIG. 4A, the first sensor 408a is in electronic communication with a power supply 314 through a line of electronic communication 406a between the first sensor 408a and the power supply 314. The first sensor 408a is in electronic communication with a monitor control box 306 through a line of electronic communication 412a between the first sensor 408a and the monitor control box 306. Similarly, the second sensor 408b is in electronic communication with the power supply 314 through a line of electronic communication 406b between the second sensor 408b and the power supply 314. The second sensor 408b is also in electronic communication with the MCB 306 through a line of electronic communication 412b between the second sensor 408b and the MCB 306. The sensors 408a, 408b are supplied with power through their respective lines of electronic communication 406a, 406b with the power supply 314. Furthermore, the first pressure measured by the first sensor 408a and the second pressure measured by the second sensor 408b may be transmitted to the MCB 306 through the sensors' respective lines of electronic communication 412a, 412b with the MCB 306.

One embodiment of a sensor assembly according to the invention will now be described with reference to FIG. 4B. A sensor assembly 400 comprises two flotation devices 404a, 404b attached to sensor housings 410a, 410b. The two sensor housings 410a, 410b comprise a first sensor housing 410a which supports a first sensor 408a at a first height h1 and a second sensor housing 410b which supports a second sensor 408b at a second height h2. Accordingly, the two pressure sensors are separated by a known vertical distance D, which represents the vertical component of the distance between the first and second sensors. The known vertical distance D can be calculated by subtracting the first height h1 from the second height h2. The sensor housings 410a, 410b each have at least one opening that permits the pressure sensors to be in fluid communication with a liquid if the sensor housings 410a, 410b are submerged in the liquid. For example, if floatation devices 404a, 404b are floating on the surface of liquid, the first and second sensors 408a, 408b will both be submerged at different depths in the liquid corresponding to the first height h1 and second height h2, respectively. Because the first and second sensors are at different depths in the liquid, the first sensor will measure a first pressure that is higher than a second pressure measured by the second sensor. These pressures can then be used in conjunction with the known vertical distance D to calculate the density of the liquid.

It may be desirable to increase the length of the flotation devices 404a, 404b and to increase the distance separating the flotation devices to limit the tilt in the sensor housings caused by any disturbance in the surface of the liquid. It may also be desirable to use a gyroscope to reduce tilt. Alternatively it may be desirable to measure the angle of tilt of the sensor housings, for example by using a gyroscope, so that the known vertical distance D can be calculated from the measured angle of tilt and the vertical distance between the sensors when the sensor housings are not tilted. As another alternative it may be desirable to convert pressure readings from the sensors into information regarding the depth of the sensor in a liquid by using a recently calculated density of the liquid. The information regarding the depth of the sensors could then be used to calculate an estimated angle of tilt by employing trigonometry. In calculating an estimated angle of tilt, it may be useful include one or more additional sensors at a fixed distance from one of the two sensors and not in line with the two sensors. For example, next to a first set of two sensors a second set of two sensors may be fixed a known distance from the first set of two sensors. The pressure readings may then be converted to liquid depths at each sensor using recently estimated densities. The liquid depths at each sensor may then be used to obtain an angle of tilt. Other approaches for obtaining an exact or approximate angle of tilt could also be employed.

It is desirable that the at least one opening in each of the sensor housings 410a, 410b permits sufficient fluid communication between the sensors 408a, 408b and the liquid so that the properties of the liquid in contact with the sensors inside the sensor housings 410a, 410b is substantially similar to the properties of the liquid outside the sensor housings 410a, 410b, even if, for example, the composition and the properties of the liquid are constantly changing.

Figure 4B:
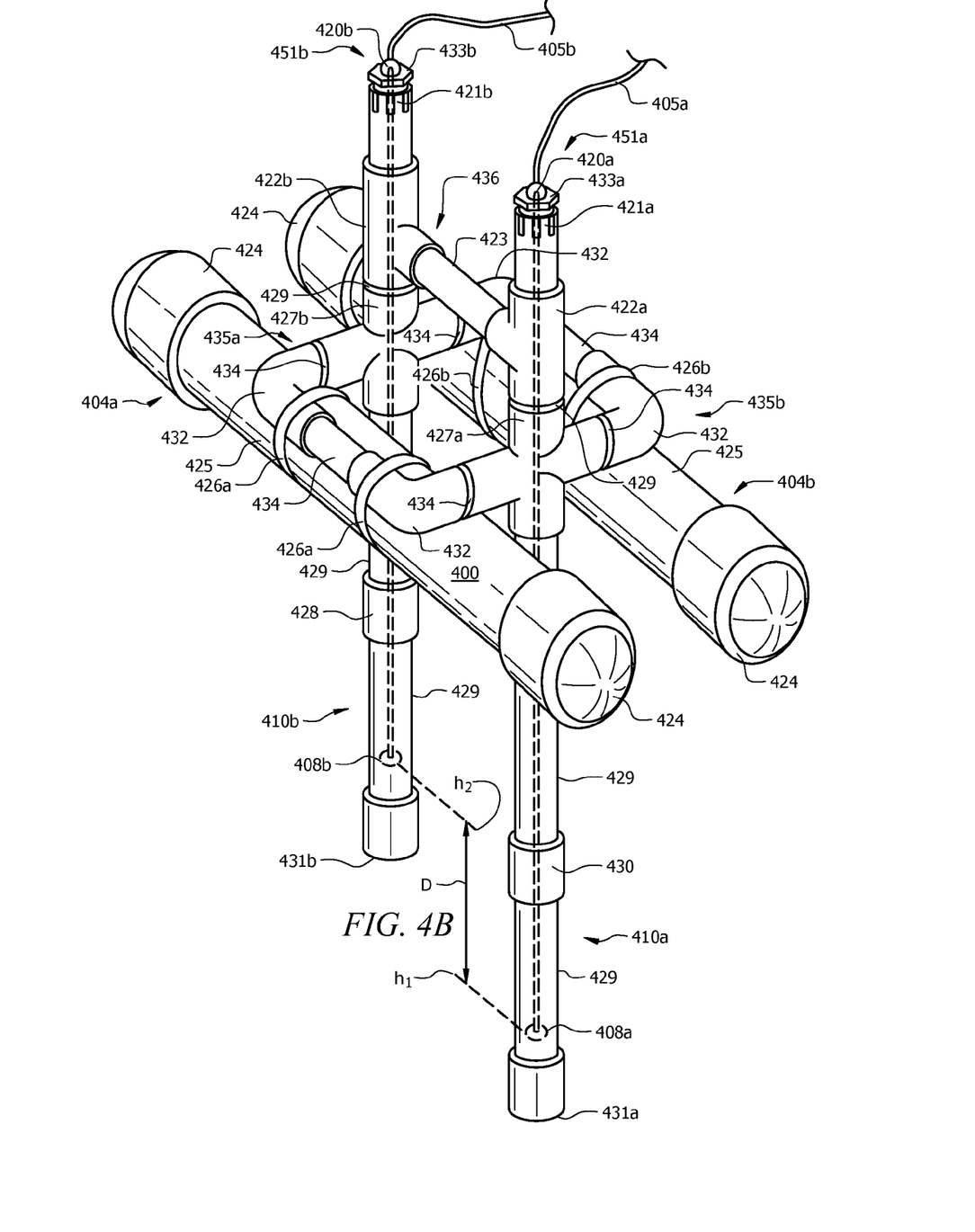
FIG. 4B depicts a perspective view of another embodiment of a sensor assembly according to the invention.

In the sensor assembly 400 depicted in FIG. 4B, the first sensor 408a is in electronic communication with a power supply through a line of electronic communication between the first sensor 408a and the power supply. The first sensor 408a is in electronic communication with an MCB through a line of electronic communication between the first sensor 408a and the monitor control box. Similarly, the second sensor 408b is in electronic communication with the power supply through a line of electronic communication between the second sensor 408b and the power supply. The second sensor 408b is also in electronic communication with the MCB through a line of electronic communication between the second sensor 408b and the MCB. The sensors 408a, 408b are supplied with power through their respective lines of electronic communication with the power supply. Furthermore, the first pressure measured by the first sensor 408a and the second pressure measured by the second sensor 408b may be transmitted to the MCB through the sensors' respective lines of electronic communication with the MCB.

In FIG. 4B, a first sheath 405a and a second sheath 405b comprise two sheaths. Sheath 405a may enclose at least one suspension cable, the line of electronic communication between the first sensor 408a and the monitor control box, the line of electronic communication between the first sensor 408a and the power supply, and a first tube between the first sensor and atmosphere. The first tube can be used by the first sensor 408a, for example, to provide atmospheric pressure to the first sensor 408a. Atmospheric pressure can be used to obtain a gauge pressure measurement, although the sensors 408a, 408b may also be set up to provide an absolute pressure measurement. Alternatively, the sheath 405a may comprise a suspension cable. Like sheath 405a, sheath 405b may enclose at least one suspension cable, the line of electronic communication between the second sensor 408b and the monitor control box, the line of electronic communication between the second sensor 408b and the power supply and a second tube between the second sensor and atmosphere. The second tube can be used by the second sensor, for example, to provide atmospheric pressure to the second sensor. Although the first sensor 408a and second sensor 408b can have substantially similar lines of electronic communication and otherwise be similarly configured, the sensors may also have different lines of electronic communication and be otherwise differently configured, for example, by including different sizes, shapes, materials, and components.

In FIG. 4B, the sensor assembly 400 comprises two flotation devices 404a, 404b attached to sensor housings 410a, 410b. The two flotation devices 404a, 404b comprise a first flotation device 404a and a second flotation device 404b.

The two sensor housings 410a, 410b comprise a first sensor housing 410a which supports a first sensor 408a at a first height h1 and a second sensor housing 410b which support a second sensor 408b at a second height h2. The first and second sensors 408a, 408b are pressure sensors in the sense that they are able to measure at least a fluid's pressure. When the sensor assembly 400 is being used to obtain a density measurement of a fluid, the sensor housings 410a, 410b are at least partially submerged in the fluid so that the first sensor 408a is submerged to a first depth in the fluid corresponding to the first height h1 and the second sensor 408b is submerged to a second depth in the fluid corresponding to the second height h2. Then, the first pressure sensor will measure a first pressure measurement corresponding to the fluid pressure at the first height h1 and the second sensor 408b will measure a second pressure measurement corresponding to the fluid pressure at the second height h2.

The sensor housings 410a, 410b are both constructed from PVC piping and fittings, although in another embodiment the sensor housings may be constructed from other appropriate materials, for example plastics or welded metals, such as stainless steel. The first sensor housing 410a is longer than the second sensor housing 410b so that the first and second pressure sensors 408a, 408b may be supported at the first and second heights h1 and h2, respectively. From bottom to top, the first sensor housing 410a comprises a first bottom end cap 431a, a pipe 429, a first coupling 430, a pipe 429, a first cross fitting 427a, a pipe 429, a first T fitting 422a, and first top end cap 451a. Although, for example, the first coupling 430 need not be present. However, if the first coupling 430 is present, it may be threaded to aid in adjusting the separation between the two sensors 408a, 408b. The first top end cap 451a may be used to hold the first sensor 408a in place. From bottom to top, the first top end cap 451a comprises a first PVC adapter 421a with one non-threaded end and one threaded end, a first threaded PVC plug 433a with an opening for the first sheath 405a, and a first seal 420a between the first threaded PVC plug 433a and the first sheath 405a. The first seal 420a may, for example, comprise a ceramic material, foam, plastic, rubber, cork, glue, or another material to create a snug fit between the first threaded PVC plug 433a and the first sheath 405a. This snug fit, for example, may fix the first sheath 405a in place with respect to the first sensor housing 410a. In one embodiment, the first seal 420a may, for example, comprise a PVC waterproof wire nut. Because the first sheath 405a may comprise or enclose a suspension cable that suspends the first sensor 408a, the first sheath 405a may be used in conjunction with a second sheath 405b and the first and second sensors housings 410a, 410b to space the first and second sensors 408a, 408b at a substantially known distance or even a substantially known vertical distance.

From bottom to top, the second sensor housing 410b comprises a second bottom end cap 431b, a pipe 429, a second coupling 428, a pipe 429, a second cross fitting 427b, a pipe 429, a second T fitting 422b, and a second top end cap 451b. Although, for example, the second coupling 428 need not be present. However, if the second coupling 428 is present, it may be threaded to aid in adjusting the separation between the two sensors 408a, 408b. The second top end cap may be used to hold the second sensor 408b in place. From bottom to top, the second top end cap 451b comprises a second PVC adapter 421b with one non-threaded end and one threaded end, a second threaded PVC plug 433b with an opening for the second sheath 405b, and a second seal 420b between the second threaded PVC plug 433b and the second sheath 405b. The second seal 420b may, for example, comprise foam, plastic, rubber, cork, glue, or another material to create a snug fit between the second threaded PVC plug 433b and the second sheath 405b. This snug fit, for example, may fix the second sheath 405b in place with respect to the second sensor housing 410b. In one embodiment, the second seal 420b may, for example, comprise a PVC waterproof wire nut. Because the second sheath 405b may comprise or enclose a suspension cable that suspends the second sensor 408b, the second sheath 405b may be used in conjunction with the first sheath 405a and the first and second sensor housings 410a, 410b to space the first and second sensors 408a, 408b at a substantially known distance or even a substantially known vertical distance.

Although the first sensor housing 410a and second sensor 410b may have substantially similar components and otherwise be similarly configured, the sensor housings 410a, 410b may also have different components and be otherwise differently configured, for example, pipe 429 may be cut to different lengths and may slide completely through a cross fitting and a T fitting rather than being attached to opposite ends of the cross fitting and T fitting.

In the embodiment of the sensor assembly 400 shown in FIG. 4B, the flotation devices 404a, 404b that support the sensor housings 410a, 410b are symmetrical. From front to back, the flotation devices 404a, 404b comprise an end cap 424, a pipe 425, and an end cap 424. Although the flotation devices 404a, 404b may have substantially similar components and otherwise be similarly configured, the flotation devices 404a, 404b may also have different components and be otherwise differently configured.

In the embodiment of the sensor assembly 400 shown in FIG. 4B, the first sensor housing 410a is in front of the second sensor housing 410b. Because both sensor housings 410a, 410b are oriented substantially vertically, they are also oriented substantially parallel. The first sensor housing 410a is secured in a substantially parallel orientation to the second sensor housing 410b by three configurations of PVC piping and fittings. Beginning with the left side of the first sensor housing 410a as shown in FIG. 4B, the first configuration 435a of PVC piping and fittings comprises, from front to back, the first cross fitting 427a on the first sensor housing 410a, pipe 434, a 90 degree elbow 432, pipe 434, a 90 degree elbow 432, pipe 434, and the second cross fitting 427b on the second sensor housing 410b. The second configuration 435b of PVC piping and fittings forms a mirror image of the first configuration 435a of PVC piping and fittings and occurs on the opposite side of the sensor housings 410a, 410b. Beginning with the right side of the first sensor housing 410a as shown in FIG. 4B, the second configuration 435b of PVC piping and fittings comprises, from front to back, the first cross fitting 427a on the first sensor housing 410a, pipe 434, a 90 degree elbow 432, pipe 434, a 90 degree elbow 432, pipe 434, and the second cross fitting 427b on the second sensor housing 410b. The third configuration 436 of PVC piping and fittings that secures the sensor housings 410a, 410b in a substantially parallel orientation comprises, from front to back in FIG. 4B, the first T fitting 422a on the first sensor housing 410a, pipe 423, and the second T fitting 422b on the second sensor housing 410b.

Together, the sensor housings 410a, 410b and the three configurations 435a, 435b, 436 of PVC piping and fittings that secure the sensor housings 410a, 410b in a substantially parallel orientation may form a combined sensor housing. As shown in FIG. 4B, the combined sensor housing is secured to the first flotation device 404a by wrapping a first two bands 426a around the first configuration 435a of PVC piping and fittings and the first flotation device 404a. Likewise, the sensor housing is secured to the second flotation device 404b by wrapping a second two bands 426b around the second configuration 435b of PVC piping and fittings and the second flotation device 404b.

The sensor assembly 400 may be comprised of substantially symmetrical components or substantially nonsymmetrical components. For example, one or more floats and one or more sensor housings may be symmetrical or non-symmetrical with respect to an axis or plane. The sensor assembly may be comprised of substantially similar components of a given type such as a pipe, or different kinds of pipe, for example pipe made from different materials. The inventor expects variations in the configuration of the sensor assembly 400 including but not limited to variations in size, shape, materials, and constituent components. As another example, the sensor assembly may not even include a sensor housing. For example, the sensors may be directly suspended in a fluid and separated by a known vertical distance by using suspension cables. As another example, the suspension cables may be tied together so that the sensors may be suspended in a fluid and separated by a known vertical distance.

Figure 4C:
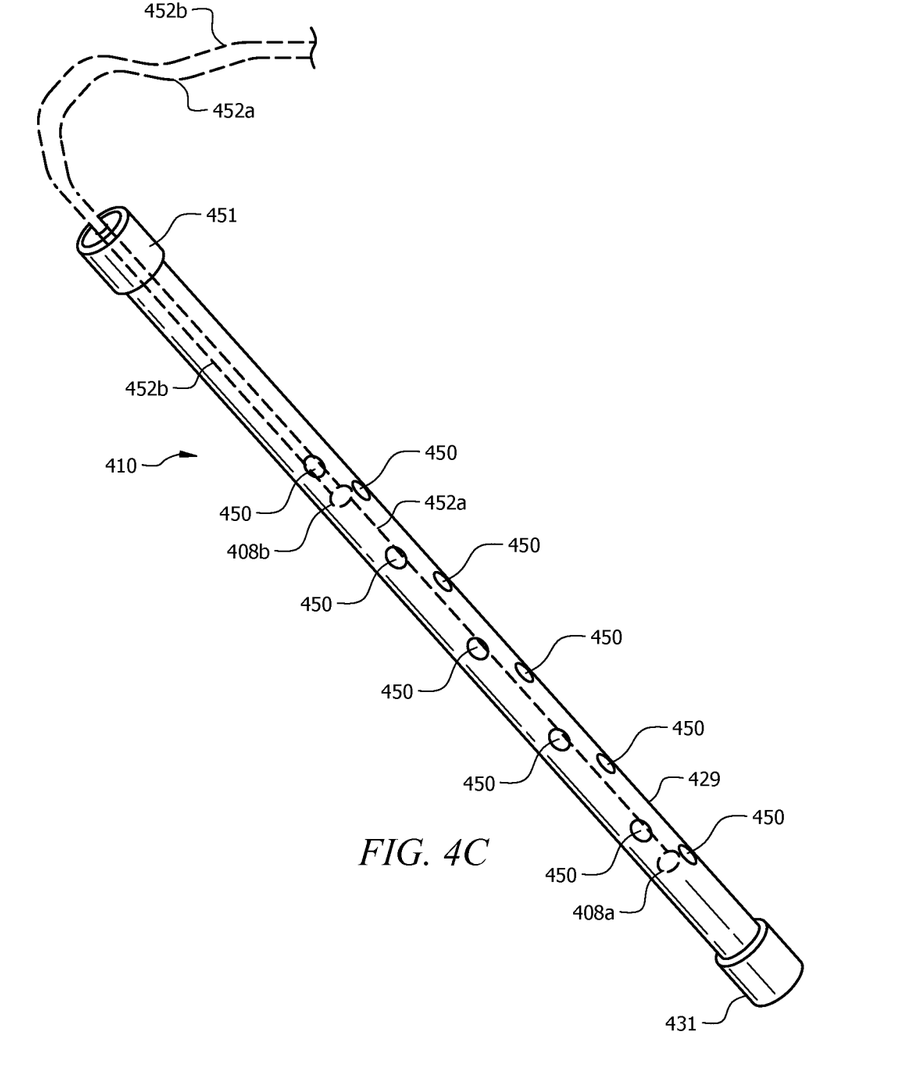
FIG. 4C depicts a perspective view of one embodiment of a sensor housing according to the invention.

One embodiment of a sensor housing according to the invention will now be described with reference to FIG. 4C. A sensor housing 410 comprises from top to bottom a top end cap 451, a PVC pipe 429, and a bottom end cap 431. The end caps may be used to help hold two pressure sensors 408a, 408b in place. The PVC pipe 429 comprises holes 450. As in FIG. 4A, and unlike FIG. 4B, the two pressure sensors 408a, 408b in FIG. 4C are both in a single sensor housing 410. If the sensor housing 410 is submerged in a liquid, the holes 450 allow the two pressure sensors 408a, 408b inside the sensor housing 410 to be in fluid communication with the liquid. The two pressure sensors 408a, 408b comprise a first pressure sensor 408a and a second pressure sensor 408b. The first pressure sensor 408a may transmit and receive electronic communication through a first cable 452a. The second pressure sensor 408b may transmit and receive electronic communication through a second cable 452b. The first and second cables, 451a, 451b extend through a hole in the top of end cap 451.

COMPARATIVE EXAMPLES

In one embodiment, the invention comprises an apparatus or system that can measure at least one of a fluid's properties to a desired accuracy. For example, the fluid may comprise a liquid, a mud, a cement, a slurry, or a solution.

In another embodiment, the invention comprises an apparatus or system that detects, records and reports information to at least one user. In one embodiment, the apparatus continuously detects, records and reports information, although in another embodiment the apparatus performs these operations intermittently. The information may be collected by at least one sensor. The information may comprise data regarding a physical or chemical property of a liquid. Examples of physical properties include but are not limited to absorption, boiling point, capacitance, color, concentration, density, electrical conductivity, melting point, solubility, specific heat, temperature, thermal conductivity, viscosity, and volume. Examples of chemical properties include but are not limited to chemical stability, enthalpy of formation, flammability, heat of combustion, and toxicity. The information may comprise data regarding a liquid, including at least one measured liquid property, for example, density, viscosity, pH, and chloride content. The apparatus or system may detect information comprising at least two pressures at two different depths in a liquid. The at least two pressures may be obtained by using two sensors. In one embodiment the sensors can provide pressures in psi, pressures in inches of water column, densities in pounds per gallon, or some combination thereof that are accurate to 0.01% of a respective measurement. Additionally, the apparatus or system may include redundant sensors, multiple sensors to measure different properties, or single sensors that measure multiple properties. The information detected by the apparatus or system may be saved by the apparatus or system, for example, for up to four years.

In one embodiment of a system according to the invention, a power supply is in electronic communication with a sensor assembly and a monitor control box. The sensor assembly is also in electronic communication with an MCB. The MCB is optionally in electronic communication with a user interface. The user interface comprises a minimum of one device capable of at least receiving information from or transmitting information to the MCB. The sensor assembly comprises at least two corrosion-resistant pressure sensors spaced apart by a known vertical distance whose end points correspond to the heights of the at least two sensors. Each of the at least two sensors may comprise a stainless steel body that houses a sensor element that comprises a ceramic material. The sensors may comprise, for example, VEGAWELL 52 pressure transmitters with suspension cables. The VEGAWELL 52 pressure transmitter can be obtained from VEGA Grieshaber KG, Am Hohenstein 113, 77761 Schiltach, Germany.

A VEGAWELL 52 pressure transmitter comprises a sensor element made from dry ceramic-capacitive CERTEC® and a base element and diaphragm made from high purity sapphire-Ceramic®. A sensor, for example a sensor comprising a VEGAWELL 52 pressure transmitter, comprises a pressure sensing facing. As used herein a facing is a surface that contacts the liquid. The pressure sensing facing may comprise, for example a diaphragm. Without wishing to be bound by theory, it is believed that via the diaphragm, a liquid's hydrostatic pressure causes a capacitance change in a measuring cell in the VEGAWELL 52. The capacitance change is then converted into an appropriate output signal, for example a current signal. In the VEGAWELL 52, the entire measuring cell consists of high purity ceramic. In addition to having excellent long-term stability, the measuring cell also has very high overload resistance.

Because the sensor element is a fluid-contacting element, for example through the pressure sensing facing, the sensor element of the sensor is subject to contact with the liquid. For example, a diaphragm in a sensor element that comprises a pressure transducer may be in direct contact with the liquid, and thus be a fluid-contacting part.

Without wishing to be bound by theory, the inventor believes that if the liquid is fouling or corrosive, for example abrasive, erosive, caustic, basic, or acidic, the sensor element can foul or corrode, causing the sensor to fail. For example, if a sensor element comprises a pressure transducer, a diaphragm in the pressure transducer may experience unacceptable levels of corrosion if it is not made from a corrosion-resistant material. Similarly, if, for example, a diaphragm in a pressure transducer is not made from a fouling-resistant material, the diaphragm may experience unacceptable levels of fouling. Furthermore, if, for example, a diaphragm in a pressure transducer is not made from an abrasion-resistant or erosion-resistant material, the diaphragm may experience abrasion or erosion, respectively. However, by using fouling-, corrosion-, abrasion-, and erosion-, caustic-, basic-pH-, and acidic-pH resistant materials, for example, dry ceramic-capacitive CERTEC® and high purity sapphire-Ceramic® for the sensor element, a fouling-, corrosion-, abrasion-, and erosion-, caustic-, basic-pH-, acidic-pH-resistant sensor may be obtained.

Although CERTEC® and high purity sapphire-Ceramic® are examples of a fouling-resistant, corrosion-resistant, abrasion-resistant, erosion-resistant, caustic-resistant, base-resistant, and acid-resistant material in the context of drilling fluid, other materials may also exhibit fouling-resistance, corrosion-resistance, abrasion-resistance, erosion-resistance, caustic-resistance, high-pH-resistance, low-pH-resistance, or some combination of these or other potentially desirable characteristics when exposed to a liquid, including but not limited to muds, cements, slurries and solutions, with fouling, corroding, abrasive, erosive or other characteristics that tend to damage a pressure sensor or impede measuring the liquid's pressure. For example, one characteristic of a diaphragm that makes it desirable is being sufficiently flexible to provide a measurable change in flex when the diaphragm is in contact with a fluid at different pressures. An example of a diaphragm characteristic that makes it resistant to exposure to harsh conditions in a fluid is being durable, at least to a desired degree. For example, diaphragms made from metals are flexible, but will also dent if hit by a solid in a liquid, for example a well cutting or a rock. In contrast, a ceramic diaphragm tends not to dent like a metal, but breaks instead. For example, the ceramic diaphragm in the VEGAWELL 52 pressure transmitter is resistant to a harsh environment, durable, measurably flexible, and hard, but tends to break rather than dent. One advantage of a diaphragm that breaks, rather than dents is that breakage will result in a pressure reading that indicates breakage has occurred. In contrast, if a metal diaphragm dents, it may result in an incorrect pressure reading, but it will not necessarily be clear that the diaphragm has been damaged or that the pressure reading is incorrect.

Besides ceramic materials, polymers or other materials with one or more desirable characteristics may be used in a sensor element or the pressure sensing facing. For example, desirable characters include but are not limited to being resistant to a harsh environment, durable, measurably flexible, hard, tending to break rather than dent, capable of being used as a measuring cell, capable of being used as a capacitor, capable of being used in conjunction with a measuring cell, and capable of being used in conjunction with a capacitor.

In one embodiment of the invention, the MCB comprises a programmable logic controller (PLC) and a computer. The programmable logical controller comprises a CPU module such as part number C0-00DD1-D, available from Automationdirect.com, 3505 Hutchinson Road, Cumming, Ga. 30040. For example, the C0-00DD1-D comprises a CPU with eight 24 VDC sink/source inputs and two isolated commons, six 5 to 27 VDC sinking outputs with 0.1 A/pt and two isolated commons, 8K steps of total program memory, Ladder Logic programming, a built-in RS232C programming port, an additional RS232C Modbus RTu/ASCII communications port that can be configured up to 115200 baud, a removable terminal block, and replacement Analogue to Digital Converter ("ADC") part number C0-16TB. However, a PLC may comprise other components and employ other configurations as well. For example, a PLC may have a different CPU, a different number, voltage, current, or type of outputs or inputs, a different amount of total program memory, different programming languages, different or additional programming or communication ports, additional components, less components, components with different configurations, and a different configuration as a whole.

The computer in the MCB may comprise an operator panel such as the G306, available from Red Lion Controls, Worldwide Headquarters, 20 Willow Springs Circle, York, Pa. 17406, USA. For example, the Red Lion G306 is powered at 24 volts direct current (VDC) and comprises a color LCD monitor, a touchscreen, a software configuration, a keypad for use with on-screen menus, LED indicators, serial ports, an ethernet port, a facility for remote web access and control, a USB port for downloading software configurations, non-volatile memory for storing software configurations, a CompactFlash mass storage device socket, and a front panel satisfying a National Electrical Manufacturers Association ("NEMA") rating of 4× and an IP Code of IP66. However, a computer may comprise other components and configurations as well. For example, a computer may be a laptop, or a desktop computer, a smart phone, a personal digital assistant ("PDA"), or other device with various configurations.

In one embodiment, the invention comprises a single sensor housing that houses at least two pressure sensors separated by a known vertical distance. In another embodiment, each of the at least two pressure sensors separated by a known vertical distance may be housed in a separate sensor housing. In addition to pressure sensors, one or more sensor housings may house other sensors. Generally speaking, a sensor housing may substantially or partially contain sensors, protect sensors and maintain two pressure sensors at a fixed distance relative to each other. However, a device as simple as a rigid body of sufficient length may also be used to maintain the sensors at a fixed relative distance. For example, the fixed relative distance may be 12 inches or 24 inches. However, different lengths may also be used. For example, the lengths may be less than 12 inches, between 12 inches and 24 inches, or greater than 24 inches. Several factors influence the length, for example, a minimum known vertical distance necessary between at least two pressure sensors to obtain reliable density measurements for a liquid, and a maximum known vertical distance between the at least two pressure sensors such that the pressure sensors may all be submerged in the liquid.

In one embodiment, the invention comprises an apparatus or system that can measure density accurately to 0.0001 pounds per gallon and includes a device capable of visually displaying density measurements with a one's digit and five decimal places, for example "0.00000", if desired. For example, in one embodiment, the pressure transmitters are so sensitive that they can detect a pressure change in air due to wind or due to being blown on by a person. In one embodiment, the apparatus or system provides real-time read-outs of density measurements while the apparatus or system is in situ. Accordingly, this eliminates the need for calling out mud weight over intercoms.

In one embodiment, the invention comprises an electronic device for determining the density of drilling mud. The device comprises two transducers submerged in a liquid at a fixed vertical distance apart. The device provides a digital read-out of two pressures measured by the two transducers. The device uses an algorithm to calculate the difference in pressure detected at the two transducers. The result of the calculation is then shown in a digital read-out. The device calculates the difference in pressures approximately 10 times per second. The difference in pressure is then used in combination with the fixed vertical distance to calculate the density of the liquid. The device digitally displays the density. The device calculates the difference in pressures approximately 10 times per second.

In one embodiment, when an apparatus or system according to the invention is placed at a drilling site, probes are placed in a mud tank and data is immediately calculated by micro-processors and transmitted to a smart phone, portable device, computers on site, or to remote corporate offices. For example, while in situ, the apparatus or system may wirelessly transmit real-time data regarding the mud in a downhole feed mud tank to a driller floor monitor, a company man on a drill site, and a corporate office monitoring a well. Furthermore, the apparatus or system may permit a driller to make real-time decisions about mud conditions.

One embodiment of the invention provides graphs that show pressure at any point in the drilling process. These graphs may be provided, for example, as electronic graphs that a user may download.

Another embodiment of the invention includes alarms that can be set to notify a driller when mud is too heavy or too light for the condition down-hole. For example, the alarm may be set by the driller with high and low limits. In one embodiment, these alarms can be used to reduce the liability associated with drilling a well.

In one embodiment the invention comprises an apparatus or system that is autonomous. For example, after connecting the apparatus or system to a power supply and setting up the apparatus or system in situ, no additional actions are required for the in situ apparatus or system to continuously measure, record, and transmit density pressures. As another example, after setting up an apparatus or system comprising its own power supply, no additional actions are required for the in situ apparatus or system to continuously measure, record, and transmit density pressures. As another example, after setting up an apparatus or system in situ, no additional actions, apart from maintenance, for example calibrating, cleaning, repairing, or replacing a component, are required for the in situ apparatus or system to substantially continuously measure, record, and transmit density pressures.

In one embodiment, the invention comprises an apparatus or system that requires no supply of external power. For example, the invention may use solar power or batteries, or fuel cells or any combination thereof. In one embodiment, the apparatus or system can operate for 24 hours without a solar charge. This permits the invention to be operated, for example, without needing to provide a separate source of power at a drill site. This is feasible, in part, because the apparatus or system requires little power, for example, using approximately 24 Watts of power or less. The embodiment may also comprise back up batteries that can, for example, power the invention for 36 hours.

In another embodiment, the invention comprises an apparatus or system that is portable, for example, capable of being carried, slid, or rolled on wheels. The apparatus, the system or any constituent components may be portable. Accordingly, the invention may comprise handles, sleds, or wheels. The invention may also be light weight. For example, one embodiment of the invention comprises a unit, including probes, that weighs less than 95 pounds. Additionally, the invention may be compact. For example, one embodiment of the invention comprises a unit that occupies less than 10 square feet. In another example, an embodiment of the invention comprises a sensor assembly that occupies less than 10 square feet. In yet another example, the invention comprises a monitor control box, sensor assembly and power supply and occupies less than 10 square feet of space. Due to its compact size and light weight, one embodiment of the invention can be flown to remote locations by light aircraft or shipped at low costs.

In another embodiment of the invention, all components are weather proof and sensors are durable enough to withstand the demands of an oil drilling site. For example, in one embodiment of the invention, the sensors are mud probes made from durable materials. In another embodiment, the sensors are made from the toughest industrial materials available. In another embodiment the sensors comprise ceramic and stainless steel components. In one embodiment, the sensors comprise VEGAWELL 52 pressure transmitters with suspension cables. For example, a VEGAWELL 52 pressure transmitter comprises a sensor element made from dry ceramic-capacitive CERTEC® and a base element and diaphragm made from high purity sapphire-Ceramic®. Because the sensor element is a fluid-contacting element, it is subject to contact with the liquid. For example, a diaphragm in a sensor element that comprises a pressure transducer may be in direct contact with the liquid, and thus be a fluid-contacting part. If the liquid is corrosive or fouling, the sensor element can corrode or foul, causing the sensor to fail. For example, if a sensor element comprises a pressure transducer, a diaphragm in the pressure transducer may experience unacceptable levels of corrosion if it is not made from corrosion-resistant material.

In another embodiment, the invention provides a method comprising the steps of pooling a corrosive liquid, inserting into the liquid an apparatus comprising at least two pressure sensors separated by a known vertical distance so that the at least two pressure sensors are submerged in the liquid, using the at least two pressure sensors to detect at least two pressures of the liquid corresponding to at least two different liquid depths, transmitting data comprising the at least two different pressures to a device capable of converting the pressure data to a density, using the device to convert the at least two different pressures into a density for the corrosive liquid, and transmitting to a user a result comprising at least the density for the corrosive liquid.

In another embodiment, the invention comprises a system or apparatus that enables real-time, continuous analysis of process variables critical to drilling mud performance while the system or apparatus is in situ with respect to a fluid being analyzed. For example, while the apparatus is in place detecting, recording, and transmitting information regarding the fluid being analyzed, the apparatus or system can provide real-time, continuous information regarding process variables, for example drilling mud density, that are critical to drilling mud performance. In one embodiment the system or apparatus, in situ, is capable of transmitting real-time, continuous pressure measurements from the sensors, which pressure measurements are convertible to a density measurement of a corrosive liquid.

While this invention has been particularly shown and described with reference to preferred embodiments, it will be understood by those skilled in the art that various changes in form and detail may be made therein without departing from the spirit and scope of the invention. The inventor expects skilled artisans to employ such variations as appropriate, and the inventor intends the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ADDITIONAL EMBODIMENTS

Various additional embodiments of the invention will now be described

One embodiment is an apparatus for measuring in situ the density of a corrosive liquid, such as drilling mud, said apparatus comprising: at least two corrosion-resistant pressure sensors separated by a known vertical distance on the apparatus, wherein the at least two pressure sensors comprise corrosion-resistant fluid-contacting parts. In another embodiment, the corrosion-resistant fluid-contacting parts comprise a ceramic material. In another embodiment, the ceramic material is selected from the group consisting of dry ceramic-capacitive CERTEC® and high purity sapphire-Ceramic®.

In another embodiment, the apparatus, in situ, is capable of transmitting real-time, continuous pressure measurements from the sensors, which pressure measurements are convertible to a density measurement of the corrosive liquid.

In another embodiment, the at least two pressure sensors are fixed to at least one rigid body, said rigid body comprising a float and at least one sensor housing. In another embodiment, the at least two pressure sensors are housed in at least one sensor housing. In another embodiment, the at least two pressure sensors are housed in two separate sensor housings. In another embodiment, the at least one sensor housing contains at least one pressure sensor, wherein further said sensor housing is attached to said float such that when the apparatus is in situ the sensor housing is submerged in the liquid below the float. In another embodiment, said sensor housing contains at least two sensors spaced a vertical distance apart in the housing such that each sensor occupies a different vertical position in the liquid when the apparatus is in situ.

In another embodiment, the apparatus further comprises at least one redundant pressure sensor.

In another embodiment, the apparatus further comprises a sensor for measuring a physical or chemical property of the liquid. In another embodiment, the apparatus further comprises at least one additional sensor for measuring a fluid property selected from the group consisting of pH, viscosity, salinity, chloride content, and temperature.

In another embodiment, the apparatus further comprises a power supply.

In another embodiment, the apparatus further comprises an electronic communication with a device to convert raw data provided by the sensors.

In another embodiment, the rigid body comprises PVC pipe.

In another embodiment, the pressure sensors comprise a stainless steel casing and a ceramic pressure sensing facing.

One embodiment of the invention is a system for determining in real-time the density of a drilling mud, said system comprising: a sensor assembly, a power supply in electronic communication with said sensor assembly, a computational device in electronic communication with said sensor assembly, a user interface in electronic communication with said computational device, wherein said sensor assembly houses at least two corrosion-resistant pressure sensors, and wherein further each pressure sensor is located in a fixed location on the sensor assembly providing a known vertical distance between the two sensors. In another embodiment, the pressure sensors comprise a ceramic facing. In another embodiment, the computational device comprises a computer. In another embodiment, the computer comprises a CPU. In another embodiment, the computational device further comprises a programmable logic controller in electronic communication with the at least two sensors and the computer.

In another embodiment, the power supply comprises a battery box in electronic communication with a solar panel. In another embodiment, the battery box comprises a power converter and a battery, wherein further the power converter is in electronic communication with the battery, the solar panel, the computer, and the programmable logic controller.

In another embodiment, the at least two sensors are in wireless communication with the programmable logic controller.

In another embodiment, the computational device comprises a wireless communication device in electronic communication with the user interface. In another embodiment, the user interface is a cellular device.

One embodiment of the invention is a method for measuring physical properties, including at least the density, of a corrosive liquid, such as drilling mud, said method comprising the steps of: a) pooling a corrosive liquid; b) inserting into the liquid an apparatus comprising at least two corrosion resistant pressure sensors that are separated by a known vertical distance on the apparatus; c) detecting a reading from each of two said sensors corresponding to the pressure experienced by each sensor while in the liquid, said reading comprising raw data provided by each sensor; d) transmitting said raw data to a device; e) using the device to convert the raw data into a density value for the corrosive liquid; and f) transmitting said density value to a user interface. In another embodiment, additional sensors are used at step b). In another embodiment, said additional sensors detect raw data used in step c) related to the pH of the liquid. In another embodiment, said additional sensors detect raw data used in step c) related to the viscosity of the liquid. In another embodiment, said additional sensors detect raw data used in step c) related to the salinity of the liquid.

In another embodiment, the user interface is co-located with the device of step d). In another embodiment, the user interface is remote from the device of step d). In another embodiment, the user interface is a cellular device.

I claim:

1. A system for measuring in situ the density of a drilling mud in combination with a drilling well mud tank, said system comprising:
    at least two corrosion-resistant pressure sensors separated by a known vertical distance on the system,
    wherein the at least two pressure sensors comprise corrosion-resistant fluid-contacting parts comprising a pressure sensing facing, said pressure sensing facing comprising a ceramic material,
    wherein the at least two pressure sensors are fixed to at least one rigid body, said rigid body comprising a float that floats on the surface of the drilling mud in the drilling well mud tank and at least one sensor housing attached to said float such that when the system is in situ the sensor housing is submerged in the drilling mud below the float, and
    wherein said sensor housing contains said at least two sensors spaced a vertical distance apart in the housing such that each sensor occupies a different vertical position in the drilling mud when the system is in situ.

2. The system of claim 1, wherein the ceramic material is a high purity sapphire ceramic material.

3. The system of claim 1, wherein the system comprises a communication device for transmitting, in situ, real-time, continuous pressure measurements from the sensors, which pressure measurements are convertible to a density measurement of the drilling mud.

4. The system of claim 1, wherein the at least two pressure sensors are housed in two separate sensor housings.

5. The system of claim 1, wherein the system further comprises at least one redundant pressure sensor.

6. The system of claim 1, further comprising a sensor for measuring a physical or chemical property of the drilling mud.

7. The system of claim 1, wherein the system further comprises at least one additional sensor for measuring a fluid property selected from the group consisting of pH, viscosity, salinity, chloride content, and temperature.

8. The system of claim 1, further comprising a power supply.

9. The system of claim 1, further comprising an electronic communication with a device to convert raw data provided by the sensors.

10. The system of claim 1, wherein the rigid body comprises plastic pipe.

11. The system of claim 10, wherein the rigid body comprises PVC pipe.

12. The system of claim 1, wherein the rigid body comprises welded metal pipe.

13. The system of claim 12, wherein the rigid body comprises stainless steel pipe.

14. The system of claim 1, wherein the pressure sensors comprise a stainless steel casing.

* * * * *